United States Patent
Kalhorn et al.

(10) Patent No.: US 11,813,131 B2
(45) Date of Patent: *Nov. 14, 2023

(54) SUCTION DE-CLOGGER SYSTEM AND METHOD

(71) Applicant: MUSC FOUNDATION FOR RESEARCH DEVELOPMENT, Charleston, SC (US)

(72) Inventors: Stephen P. Kalhorn, Mount Pleasant, SC (US); Mark E. Semler, Mount Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 32 days.

This patent is subject to a terminal disclaimer.

(21) Appl. No.: 17/410,363

(22) Filed: Aug. 24, 2021

(65) Prior Publication Data

US 2021/0379270 A1 Dec. 9, 2021

Related U.S. Application Data

(63) Continuation of application No. 15/752,404, filed as application No. PCT/US2016/047309 on Aug. 17, 2016, now Pat. No. 11,097,036.

(Continued)

(51) Int. Cl.
*A61C 17/06* (2006.01)
*A61M 1/00* (2006.01)
*A61B 90/70* (2016.01)

(52) U.S. Cl.
CPC .............. *A61C 17/06* (2019.05); *A61B 90/70* (2016.02); *A61M 1/84* (2021.05); *A61B 2090/701* (2016.02); *A61M 2209/10* (2013.01)

(58) Field of Classification Search
CPC ... A61C 17/06; A61B 90/70; A61B 2090/701; A61B 2217/005; A61M 1/84;
(Continued)

(56) References Cited

U.S. PATENT DOCUMENTS

| 5,595,172 | A | 1/1997 | Reese |
| 8,246,752 | B2 | 8/2012 | Boyle, Jr. |

(Continued)

FOREIGN PATENT DOCUMENTS

| EP | 2328632 | 6/2011 |
| WO | 2010021775 | 2/2010 |

OTHER PUBLICATIONS

Office Action dated Feb. 7, 2020 for U.S. Appl. No. 15/752,404 (pp. 1-6).

(Continued)

*Primary Examiner* — Duy Vu N Deo
*Assistant Examiner* — Christopher Remavege
(74) *Attorney, Agent, or Firm* — Riverside Law LLP

(57) ABSTRACT

A declogging assembly (20) is configured for use with a suction conduit (10). The suction conduit has a head (14) at a first end (15) and a vacuum tube connection (16) at a second end (17). The assembly includes a body (30). The body defines a first aperture (32), a second aperture (34), and a third aperture (36). The assembly also includes a plug (40) disposed within the body (30). The plug has a surface (42) configured to contact the head (14) of the suction conduit (10) so as to move the plug from a first position, in which the first aperture (32) is in fluid communication with the second aperture (34), to a second position, in which the first aperture (32) is in fluid communication with the third aperture (36). The assembly (20) also includes a biasing member (50) configured to bias the plug into the first position.

8 Claims, 15 Drawing Sheets

Related U.S. Application Data

(60) Provisional application No. 62/206,032, filed on Aug. 17, 2015.

(58) Field of Classification Search
CPC ............ A61M 2209/10; A61M 39/223; A61M 39/225; A61M 2039/2473; B08B 9/027
See application file for complete search history.

(56) References Cited

U.S. PATENT DOCUMENTS

| | | | |
|---|---|---|---|
| 8,726,453 | B2 | 5/2014 | Berry |
| 9,694,119 | B2 | 7/2017 | Cheng |
| 10,188,482 | B2 | 1/2019 | Reinard |
| 2004/0221904 | A1 | 11/2004 | Usher |
| 2009/0264833 | A1 | 10/2009 | Boyle, Jr. |
| 2012/0144608 | A1 | 6/2012 | Berry |
| 2014/0250615 | A1* | 9/2014 | Berry ..................... A61B 90/70 15/104.05 |
| 2014/0352724 | A1 | 12/2014 | Meyer |
| 2015/0073364 | A1* | 3/2015 | Cheng ..................... A61M 1/74 604/319 |
| 2015/0273121 | A1 | 10/2015 | Olivero |
| 2015/0343182 | A1 | 12/2015 | Vazales |
| 2016/0001036 | A1 | 1/2016 | Nickerson |
| 2016/0022127 | A1 | 1/2016 | Iwasaki |
| 2016/0100904 | A1 | 4/2016 | Frey |
| 2018/0185115 | A1 | 7/2018 | Wynkoop |
| 2018/0207397 | A1 | 7/2018 | Look |
| 2020/0229907 | A1* | 7/2020 | Duehlmeier ......... A61C 1/0038 |

OTHER PUBLICATIONS

Office Action dated Sep. 4, 2020 for U.S. Appl. No. 15/752,404 (pp. 1-7).

Notice of Allowance dated Apr. 16, 2021 for U.S. Appl. No. 15/752,404 (pp. 1-12).

* cited by examiner

SUCTION DE-CLOGGER SYSTEM AND METHOD

CROSS-REFERENCE TO RELATED APPLICATION

This application is a Continuation of U.S. patent application Ser. No. 15/752,404, filed Feb. 13, 2018, now pending, which is the National Stage of International Application No. PCT/US2016/047309, filed Aug. 17, 2016, which claims the benefit of U.S. Provisional Application No. 62/206,032, filed Aug. 17, 2015, the disclosures of which are incorporated by reference herein in their entirety.

TECHNICAL FIELD

This disclosure relates generally to systems and methods for declogging suction conduits in medical and dental applications.

BACKGROUND

Suction conduits are used to remove material such as blood and bone fragments from the operative field during surgery or other types of medical or dental procedures. During use, these conduits may become clogged, which limits the suction that may be applied to the operative field.

SUMMARY

In a first aspect of the present disclosure, a declogging assembly is configured for use with a suction conduit. The suction conduit has a conduit body with a head at a first end of the body and a vacuum tube connection at a second end. The assembly includes a body. The body defines a first aperture, a second aperture, and a third aperture. The assembly also includes a plug disposed within the body. The plug has a surface configured to contact the head of the suction conduit so as to move the plug from a first position, in which the first aperture is in fluid communication with the second aperture, to a second position, in which the first aperture is in fluid communication with the third aperture. The assembly also includes a biasing member configured to bias the plug into the first position.

In a second aspect of the present disclosure, a declogging assembly is configured for use with a suction conduit. The suction conduit has a conduit body with a head at a first end of the body and a vacuum tube connection at a second end. The assembly includes a body. The body defines a first aperture, a second aperture, and a recess disposed between the first aperture and the second aperture. The recess has a first portion and a second portion. The assembly also includes a plug disposed within the recess of the body. The plug includes a surface configured to contact the head of the suction conduit so as to move the plug from a first position, in which the plug is disposed in the first portion of the recess and the first aperture is in fluid communication with the second portion of the recess, to a second position, in which the first aperture is in fluid communication with the second aperture. The assembly also includes a biasing member configured to bias the plug into the first position.

In a third aspect of the present disclosure, a method of declogging a suction conduit includes uses a declogging assembly. The suction conduit has conduit body with a head at a first end of the body and a vacuum tube connection at a second end. The declogging assembly has a body that defines a first aperture, a second aperture, and a third aperture. The declogging assembly also has a plug disposed within the body. The plug includes a surface and a biasing member. The method includes a step of pressing the suction conduit into the third aperture such that the head of the conduit contacts the surface of the plug. The pressing step includes overcoming a biasing force of the biasing member and moving the plug from a first position, in which the first aperture is in fluid communication with the second aperture, to a second position, in which the first aperture is in fluid communication with the third aperture. The method also includes a step of removing the suction conduit from the third aperture such that the biasing force moves the plug to the first position.

In a fourth aspect of the present disclosure, a method of declogging a suction conduit includes uses a declogging assembly. The suction conduit has conduit body with a head at a first end of the body and a vacuum tube connection at a second end. The declogging assembly has a body that defines a first aperture, a second aperture, and a recess disposed between the first aperture and the second aperture. The recess has a first portion and a second portion. The declogging assembly also includes a plug disposed within the recess of the body. The plug includes a surface and a biasing member. The method includes a step of pressing the suction conduit into the second aperture such that the head of the conduit contacts the surface of the plug. The pressing step includes overcoming a biasing force of the biasing member and moving the plug from a first position, in which the plug is disposed in the first portion of the recess and the first aperture is in fluid communication with the second portion of the recess, to a second position, in which the first aperture is in fluid communication with the second aperture via a channel. The method also includes a step of removing the suction conduit from the second aperture such that the biasing force moves the plug to the first position.

BRIEF DESCRIPTION OF THE DRAWINGS

The foregoing summary, as well as the following detailed description of illustrative embodiments of the declogger systems and methods of the present application, will be better understood when read in conjunction with the appended drawings. For the purposes of illustrating the declogging assembly of the present application, there is shown in the drawings illustrative embodiments. It should be understood, however, that the application is not limited to the precise arrangements and instrumentalities shown. In the drawings.

DETAILED DESCRIPTION OF THE ILLUSTRATIVE EMBODIMENTS

Aspects of the disclosure will now be described in detail with reference to the drawings, wherein like reference numbers refer to like elements throughout, unless specified otherwise. Certain terminology is used in the following description for convenience only and is not limiting.

Figure 1:
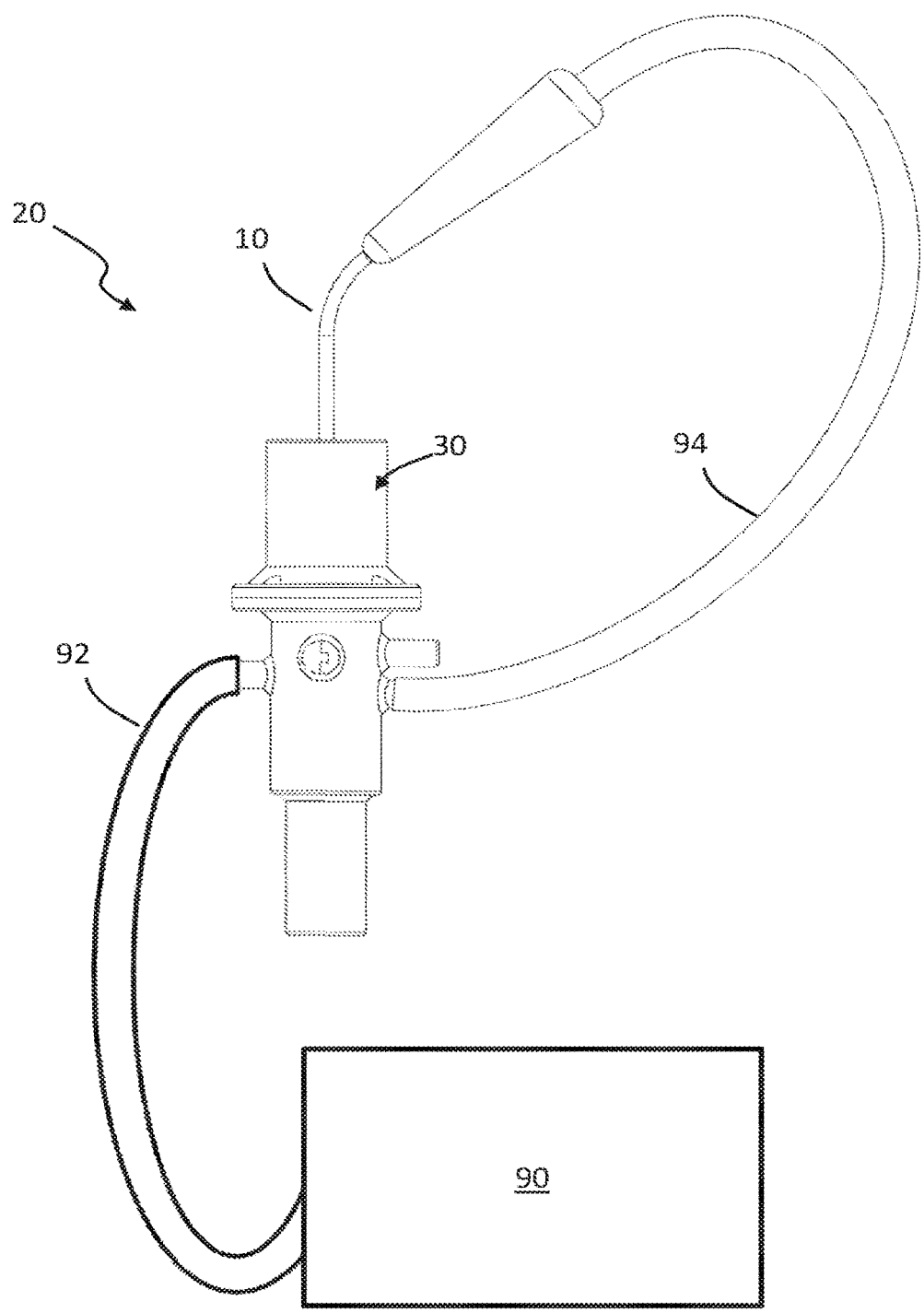
FIG. 1 is a schematic of a declogging assembly, a suction conduit and a vacuum assembly.

Referring to FIG. 1, a declogging assembly 20 is configured for use with a suction conduit 10 and a vacuum assembly 90. Declogging assembly 20 controls vacuum force from vacuum assembly 90 to the suction conduit 10. Declogging assembly 20 reverses direction of the vacuum force applied by vacuum assembly 90 so as to dislodge material that is blocking the suction conduit 10.

Figure 2A:
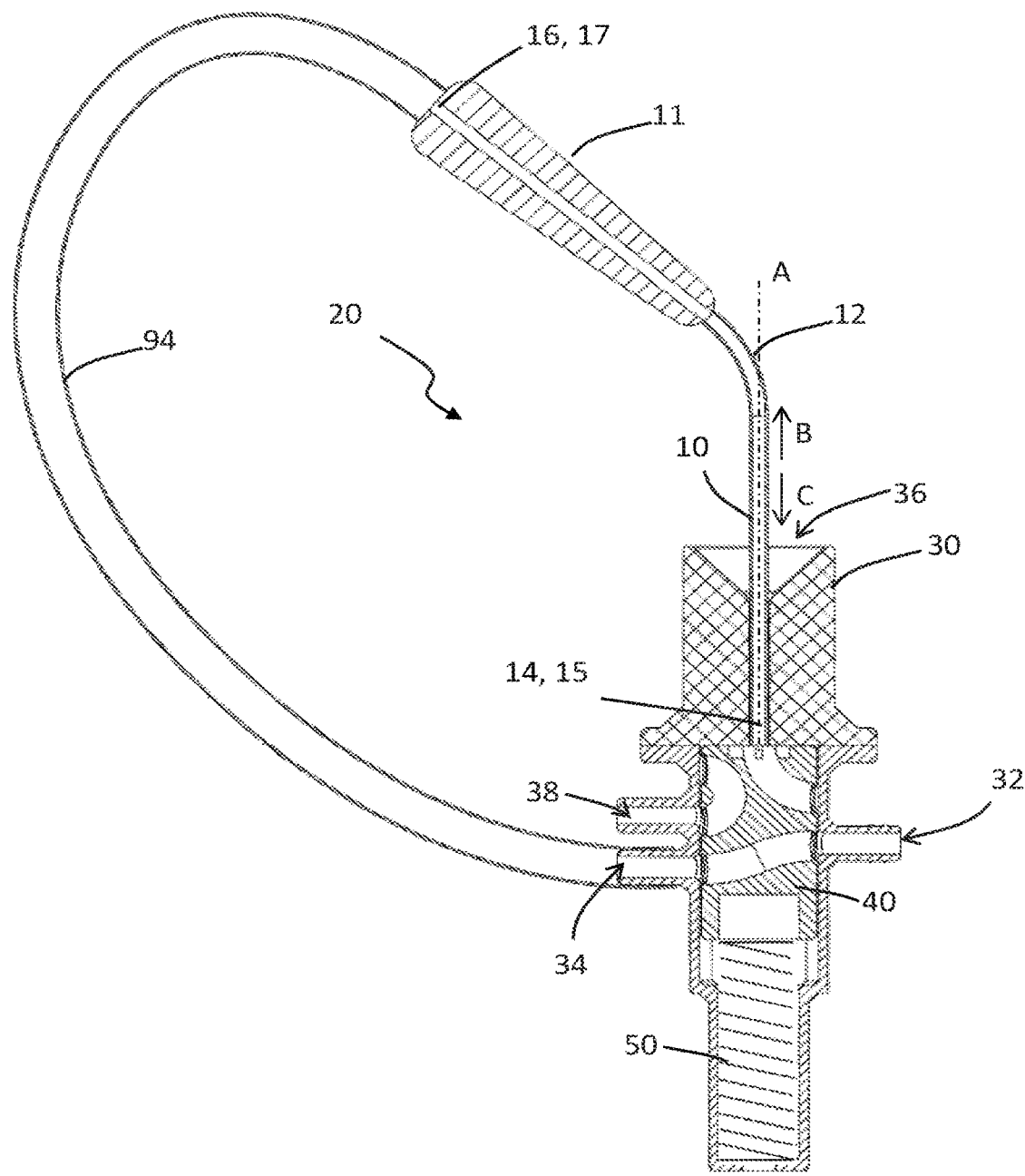
FIG. 2A is a cross-sectional view of the declogging assembly and suction conduit shown in FIG. 1, with a plug of the declogging assembly in a first position so as to provide vacuum force to the suction conduit along a first direction.
Figure 2B:
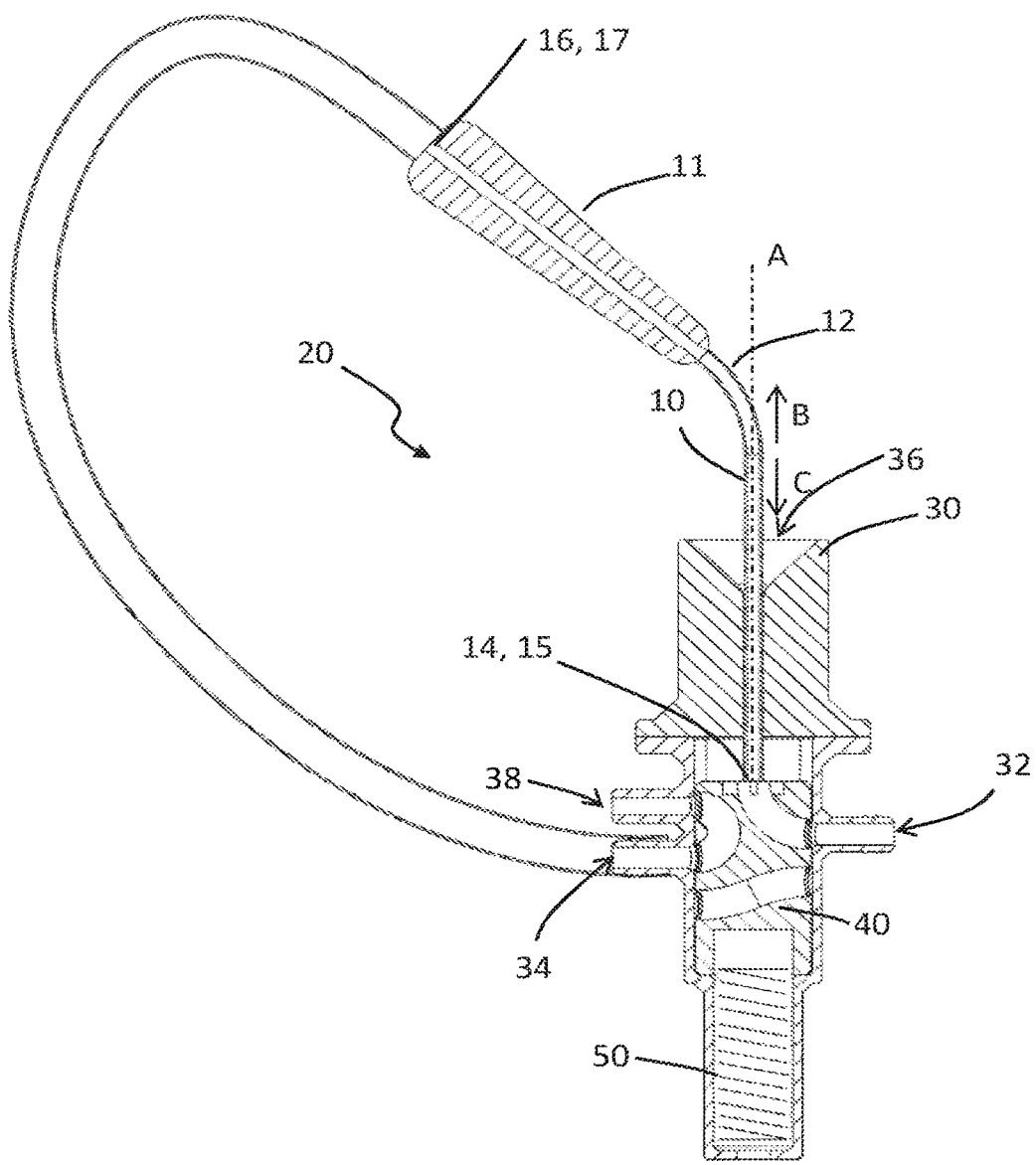
FIG. 2B is a cross-sectional view of the declogging assembly and suction conduit shown in FIGS. 1 and 2A, with the plug in a second position so as to provide vacuum force to the suction conduit along a second direction that is opposite the first direction.

With reference to FIGS. 2A and 2B, suction conduit 10 has a conduit body 12. Conduit body 12 defines a first end 15 at which a head 14 of the suction conduit 10 is disposed. Conduit body 12 further defines a second end 17 at with a vacuum tube connection 16 of the suction conduit 10 is disposed. Conduit body 12 includes at least a portion that is elongate along an axis A. Axis A defines a first direction B that extends from the head 14 towards the vacuum tube connection 16 and a second direction C that is opposite the first direction B and extends along the axis A towards the head 14. During operation, vacuum assembly 90 applies a vacuum force in the first direction B so that material may be suctioned into suction conduit 10 through the head 14 and out of the suction conduit 10 through the vacuum tube connection 16. Declogging assembly 20 is configured to reverse this vacuum force so that vacuum assembly 90 applies the force in the second direction C so that material, such that material that is clogging suction conduit 10 when the vacuum force is applied along the first direction B, may be suctioned in the second direction C away from vacuum tube connection 16 and out of the suction conduit 10 through the head 14. Suction conduit 10 may also include a handle 11 and a pressure opening 13 (shown in FIG. 5).

Figure 3A:
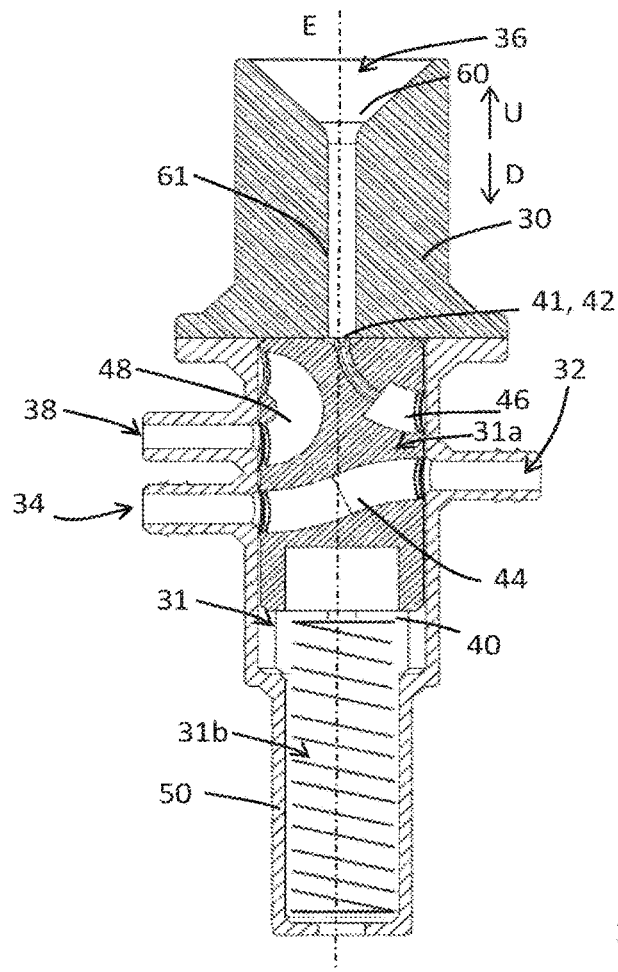
FIG. 3A is a cross-sectional view of the declogging assembly shown in FIGS. 1, 2A, and 2B, with the plug in the first position.
Figure 3B:
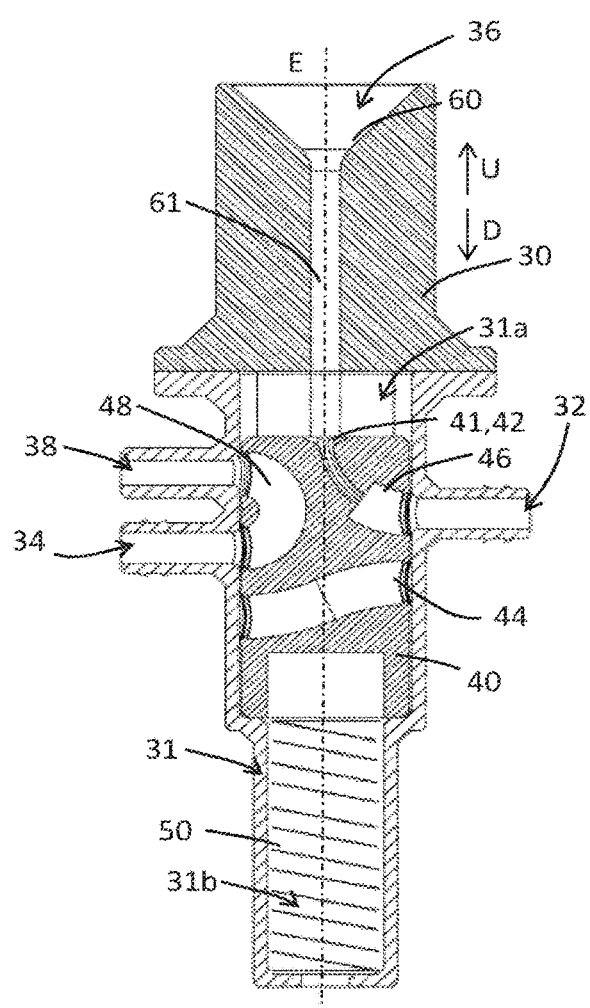
FIG. 3B is a cross-sectional view of the declogging assembly shown in FIGS. 1, 2A, 2B, and 3A with the plug in the second position.

Suction conduit 10 connects to vacuum assembly 90 via declogging assembly 20. Declogging assembly 20 includes a body 30. With reference to FIGS. 3A and 3B, body 30 is elongate along an axis E and defines a recess 31 having an first portion 31a and a second portion 31b disposed along the axis E. As shown in FIGS. 2A and 2B, when the head 14 of the suction conduit 10 is inserted into the body 30, axis A is parallel, or approximately parallel to axis E, such that an angle between axis A and axis E is no more than 10°, or no more than 5°.

Body 30 defines at least four apertures that connect recess 31 to a surrounding environment of body 30. A first aperture 32, which, for example, extends radially outward from axis E, connects the declogging assembly 20 to the vacuum assembly 90 via tube 92. A second aperture 34, which, for example, extends radially outward from axis E, connects the declogging assembly 20 to the suction conduit 10 via tube 94. A third aperture 36, which, for example, extends axially along axis E, is configured to fit the head 14 of the suction conduit 10 during declogging. Third aperture 36 may be covered by a flexible cover 62' (see FIG. 4). With reference to FIGS. 3A and 3B, third aperture 36 may include a frustoconical outer portion 60 and a cylindrical inner portion 61. The frustoconical outer portion 60 and the cylindrical inner portion 61 are configured to guide the head 14 of the suction conduit 10 into the body 30 for declogging. A fourth aperture 38, which, for example, extends radially outward from axis E, is configured to vent the declogging assembly to, for example, atmospheric pressure. The fourth aperture may be covered with a filter.

Declogging assembly 20 also includes a plug 40 moveably disposed within the recess 31 of the body 30. Plug 40 defines at least three channels that connect apertures 32, 34, 36, and 38. FIG. 3A shows plug 40 is in its first position, wherein first aperture 32 (which connects vacuum assembly 90 to declogging assembly 20 via tube 92) is in fluid communication with second aperture 34 (which connects declogging assembly 20 to the suction conduit 10 via tube 94) via first channel 44. FIG. 3B shows plug 40 is in its second position, wherein first aperture 32 is in fluid communication with third aperture 36 (which is configured to fit the head 14 of suction conduit 10) via second channel 46. FIG. 3B also depicts second aperture 34 being in fluid communication with fourth aperture 38 (which vents the declogging assembly to atmospheric pressure) via third channel 48.

Plug 40 further includes at least one flange 41 that extends into the second channel 46 and includes a surface 42. During use, the head 14 of the suction conduit 10 is configured to contact the surface 42 to move the plug 40 from its first position to its second position. The declogging assembly further includes a biasing member 50 disposed in the second portion 31b of recess 31. Biasing member 50 may be a spring that is configured to bias the plug 40 into the first position by exerting a force in an upward direction U along axis E.

Prior to insertion of the suction conduit 10, when the plug 40 is in its first position in the first portion 31a of recess 31 (shown in FIG. 3A), vacuum assembly 90 is in fluid communication with the suction conduit 10 via first channel 44. First channel 44 enables vacuum force along the first direction B relative to the suction conduit 10 so that material is suctioned into suction conduit 10 through the head 14 and out of the suction conduit 10 through the vacuum tube connection 16. The material is then suctioned through tube 94, first channel 44, and tube 92, respectively, and collected in, for example, a collection bin.

When a user inserts the suction conduit 10 into third aperture 36 and presses against surface 42 in a downward direction D along axis E (opposing the upward direction U), the biasing force of biasing member 50 may be overcome such that plug 40 moves downward into its second position in the second portion 31b of recess 31 (shown in FIG. 3B). In its second position, plug 40 enables fluid communication between first aperture 32 and third aperture 36 via second channel 46, which enables vacuum force along the second direction C relative to the suction conduit 10 so that material, such as material that is clogging suction conduit 10 when the vacuum force is applied along the first direction B, may be suctioned in the second direction C away from vacuum tube connection 16 and out of the suction conduit 10 through the head 14. The material is then suctioned through second channel 46 and out of the declogging assembly 20 through first aperture 32 and tube 92 and collected in, for example, a collection bin. Additionally, when plug 40 is in its second position, second aperture 34 is in fluid communication with aperture 38, which provides a vent, for example, to atmospheric pressure. In this way, as the vacuum force is applied in the second direction, air is pulled into declogging assembly 20 through aperture 38 and third channel 48, into tube 94. When the user releases the downward force D on the suction conduit 10, the biasing force of the biasing member 50 returns the plug 40 to its first position in the first portion 31a of the recess 31.

Figure 4:
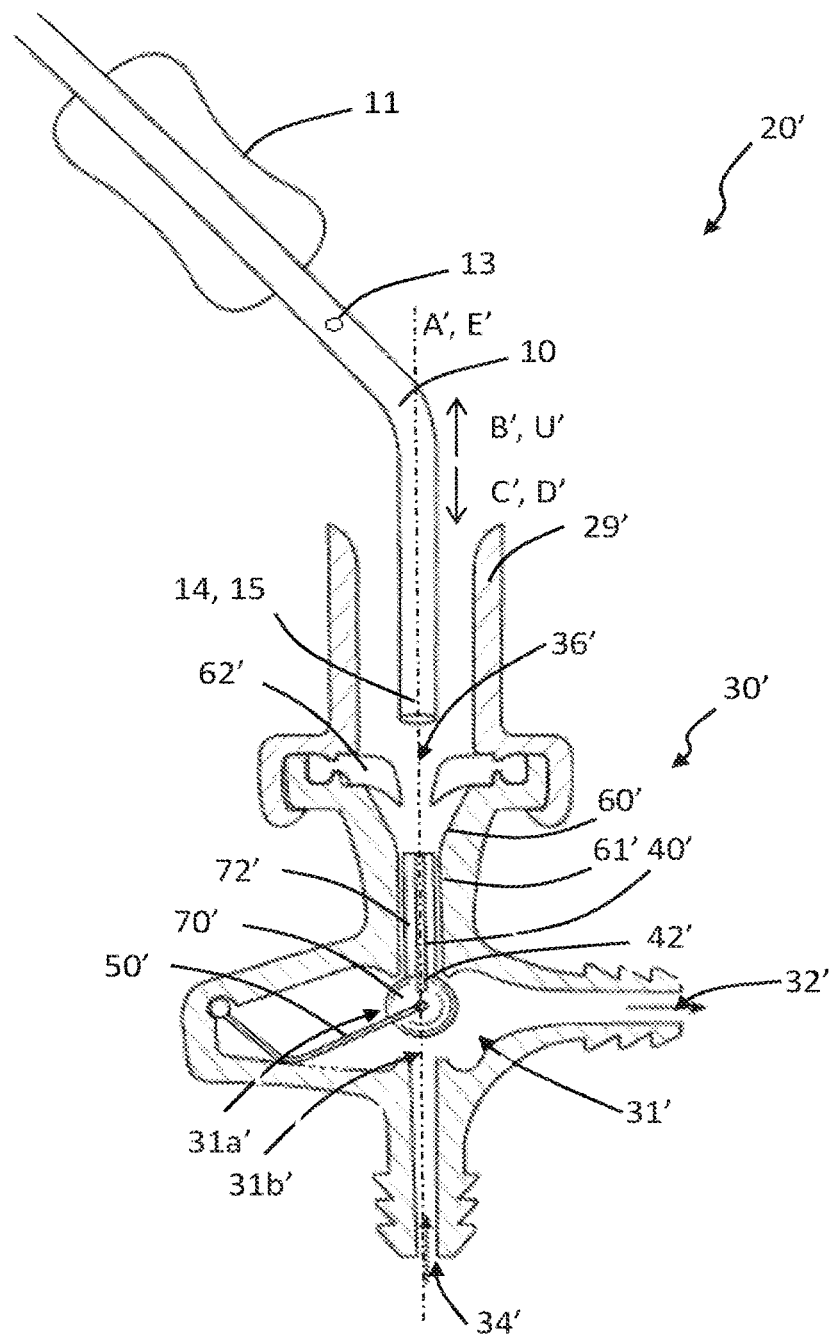
FIG. 4 is a cross-sectional view of a declogging assembly and a suction conduit with a plug of the declogging assembly in a first position so as to provide vacuum force to the suction conduit along a first direction.
Figure 5:
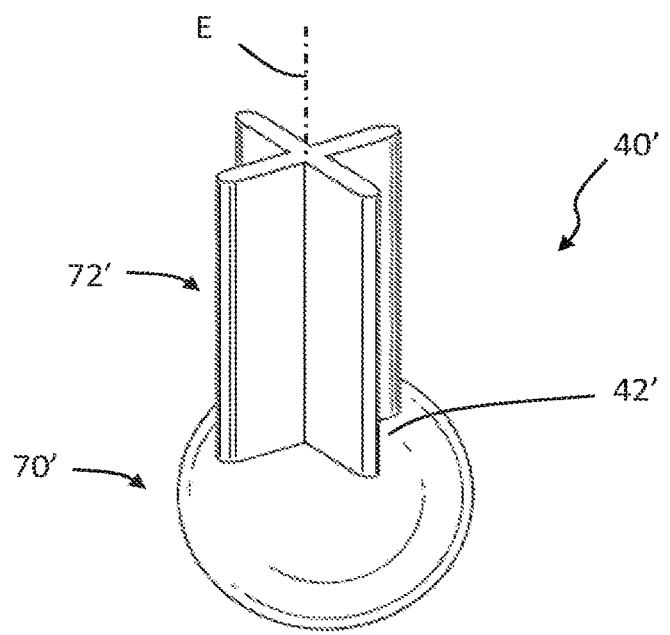
FIG. 5 is a perspective view of the plug of the declogging assembly shown in FIG. 4.

Referring now to FIGS. 4 and 5, a declogging assembly 20' is configured for use with the suction conduit 10 and the vacuum assembly 90 described in relation to FIGS. 1, 2A, and 2B. Declogging assembly 20' controls vacuum force from vacuum assembly 90 to the suction conduit 10. In conjunction with vacuum force from the vacuum assembly 90, declogging assembly 20' reverses direction of the vacuum force so as to dislodge material that is blocking the suction conduit 10.

Declogging assembly 20' includes a body 30'. Body 30' is elongate along an axis E' and defines a recess 31' having a first portion 31a' and a second portion 31b' disposed along the axis E'. When the head 14 of the suction conduit 10 is inserted into the body 30', axis A is parallel, or approximately parallel to axis E', such that an angle between axis A and axis E' is no more than 10°, or no more than 5°.

Body 30' defines at least three apertures that connect recess 31' to a surrounding environment of body 30'. A first aperture 32', which, for example, extends radially outward from axis E', connects the declogging assembly 20' to the vacuum assembly 90 via tube 92. A second aperture 34' which, for example, extends axially along axis E', connects the declogging assembly 20' to the suction conduit 10 via tube 94. A third aperture 36' which, for example, extends axially along axis E, is configured to fit the head 14 of the suction conduit 10 during declogging. Third aperture 36' may include a frustoconical outer portion 60' and a cylindrical second portion 61'. The frustoconical outer portion 60' and the cylindrical inner portion 61' are configured to guide the head 14 of the suction conduit 10 into the body 30' for declogging. Third aperture 36' may be covered by a flexible cover 62'. Flexible cover 62' minimizes flow into and out of body 30' through third aperture 36'. A splash guard 29' may be disposed above third aperture 36', which defines a channel through which suction conduit 10 passes to enter third aperture 36'.

With reference to FIG. 5, declogging assembly 20' also includes a plug 40' moveably disposed within the recess 31' of the body 30'. Plug 40' includes a base portion 70' that may, for example, be cylindrically shaped. Base portion 70' includes a surface 42' configured to contact the head 14 of the suction conduit 10 to move the plug 40' from its first position to its second position. Plug 40' further includes a flange 72' that extends from the base portion 70'. In cross-section taken along a plane that is perpendicular to axis E, flange 72' may have a cruciform shape and may be configured to fit into the conduit body 12 so as to dislodge material while providing air passage between the radially extending portions of the cruciform. Alternatively, all or part of the flange 72' may have a diameter that is greater than the recess defined by the head 14 of the suction conduit 10 such that surface 42' is defined by a top surface of the flange 72' or by a surface between the top surface of the flange 72' and the base portion 70'.

With reference again to FIG. 4, the declogging assembly 20' further includes a biasing member 50' disposed in the recess 31'. Biasing member 50' may be a spring that is configured to bias the plug 40' into the first position by exerting a force in an upward direction U' along axis E'. Prior to insertion of the suction conduit 10, the plug 40' is in its first position in the first portion 31a' of recess 31' (shown in FIG. 4). When the plug 40' is in its first position, vacuum assembly 90 is in fluid communication with the suction conduit 10 via recess 31' which, when the plug is in its first position, enables fluid communication between first aperture 32' and second aperture 34'. Vacuum force is applied along the first direction B relative to the suction conduit 10 so that material is suctioned into suction conduit 10 through the head 14 and out of the suction conduit 10 through the vacuum tube connection 16. The material is then suctioned through tube 94, declogging assembly 20', and tube 92, respectively, and collected in, for example, a collection bin.

When the user inserts the suction conduit 10 into third aperture 36' and presses against surface 42' in a downward direction D' along axis E' (opposing the upward direction U'), the biasing force of biasing member 50' may be overcome such that plug 40' moves downward into its second position in the second portion 31b' of recess 31. In its second position, plug 40' enables fluid communication between first aperture 32' and third aperture 36' via recess 31', which enables vacuum force along the second direction C relative to the suction conduit 10 so that material, such as material that is clogging suction conduit 10 when the vacuum force is applied along the first direction B, may be suctioned in the second direction C away from vacuum tube connection 16 and out of the suction conduit 10 through the head 14. The material is then suctioned through out of the declogging assembly 20' through first aperture 32' and tube 92 and collected in, for example, a collection bin. When the user releases the downward force D on the suction conduit 10, the biasing force of the biasing member 50 returns the plug 40 to its first position.

Figure 6:
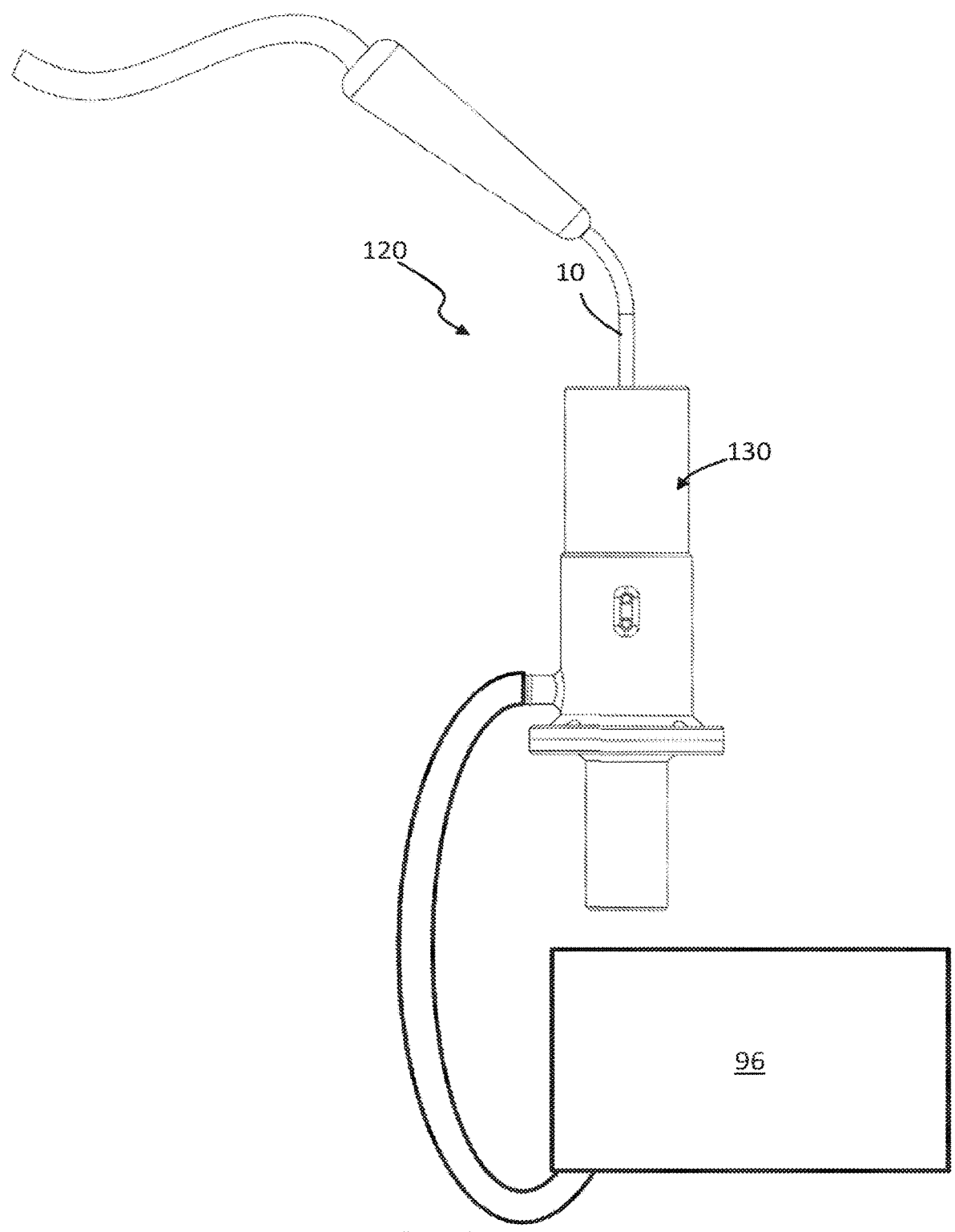
FIG. 6 is a schematic of an declogging assembly, a suction conduit, and a fluid reservoir.
Figure 7A:
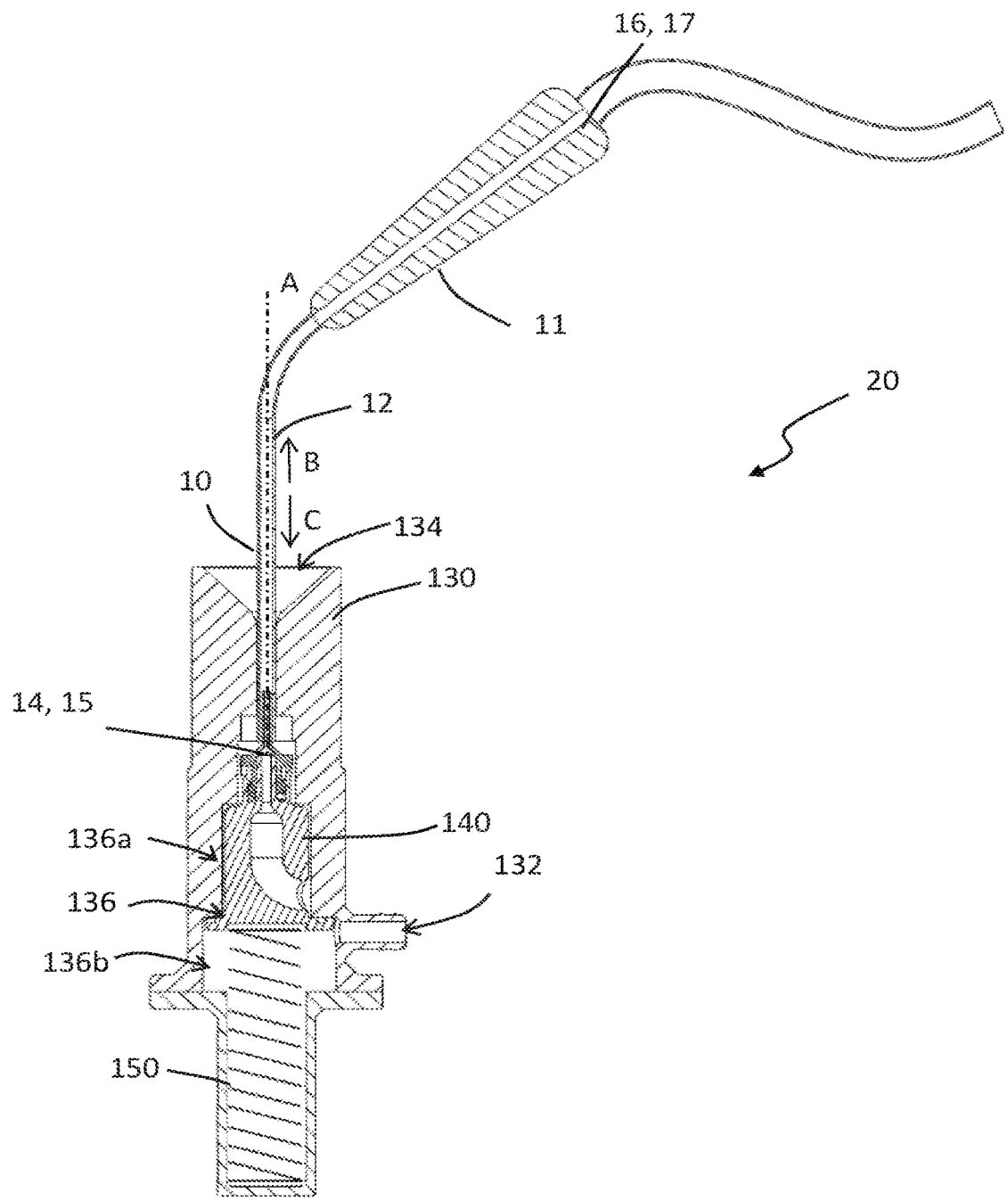
FIG. 7A is a cross-sectional view of the declogging assembly and suction conduit shown in FIG. 6, with a plug of the declogging assembly in a first position.
Figure 7B:
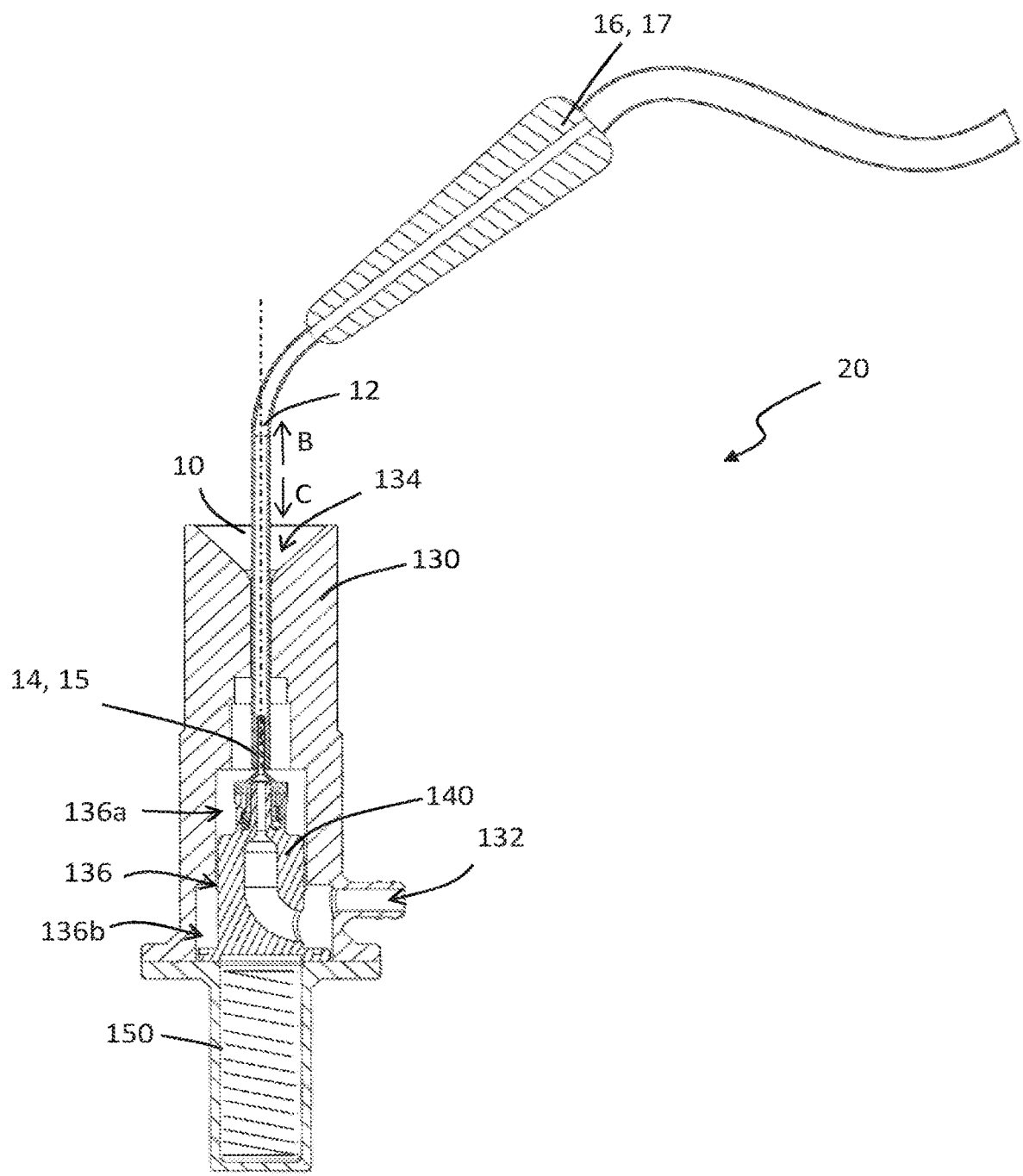
FIG. 7B is a cross-sectional view of the declogging assembly and suction conduit shown in FIGS. 6 and 7A, with the plug in a second position so as to enable fluid communication between the suction conduit and the fluid reservoir.
Figure 8A:
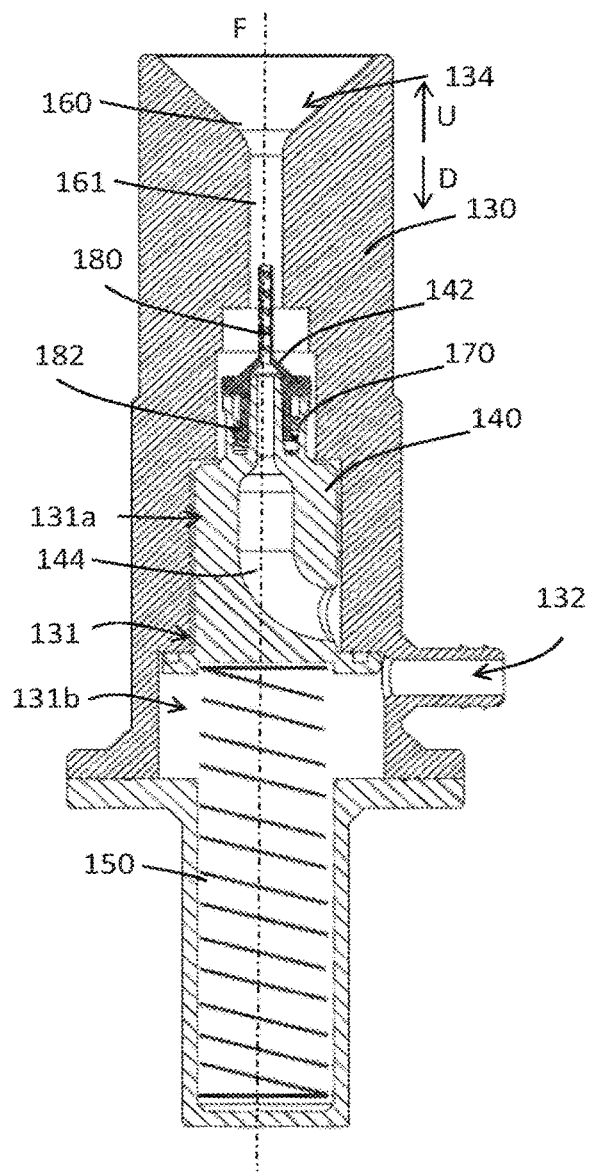
FIG. 8A is a cross-sectional view of the declogging assembly show in FIGS. 6, 7A, and 7B with the plug in the first position.
Figure 8B:
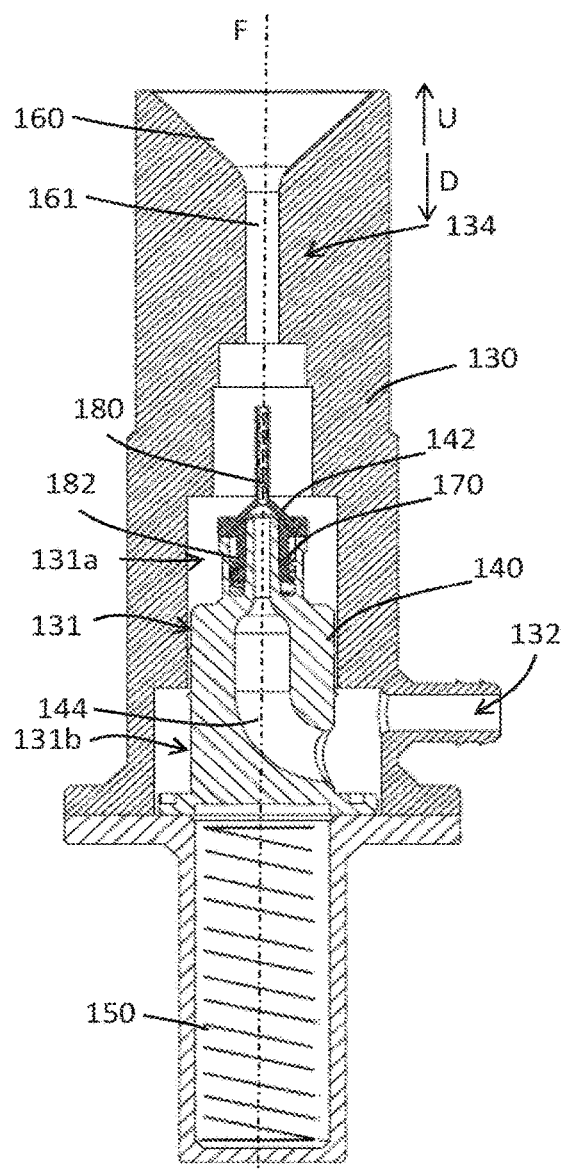
FIG. 8B is a cross-sectional view of the declogging assembly shown in FIGS. 6, 7A, 7B, and 8A with the plug in the second position.

Referring now to FIGS. 6, 7A, 7B, 8A, and 8B, a declogging assembly 120 is configured for use with the suction conduit 10 and vacuum assembly 90 described in relation to FIGS. 1, 2A, and 2B, and a fluid reservoir 96. Fluid, such as saline, water, antimicrobial solution, cleaning solutions, or a combination thereof may be disposed in fluid reservoir 96 and is used to dislodge material that may be affixed to the suction conduit 10. Fluid reservoir 96 may be, for example, a saline bag. Declogging assembly 120 controls passage of the fluid from the fluid reservoir 96 to the suction conduit 10. Declogging assembly 120 includes a body 130. With reference to FIGS. 8A and 8B, body 130 is elongate along an axis F and defines a recess 131 having an first portion 131a and a second portion 131b disposed along the axis F. As shown in FIGS. 7A and 7B, when the head 14 of the suction conduit 10 is inserted into the body 130, axis A is parallel, or approximately parallel to axis F, such that an angle between axis A and axis F is no more than 10°, or no more than 5°.

Body 130 defines at least two apertures that connect recess 131 to a surrounding environment of body 130. A first aperture 132, which, for example, extends radially outward from axis F, connects the declogging assembly 120 to the fluid reservoir 96 via a tube 98. A second aperture 134 which, for example, extends axially along axis F, is configured to fit the head 14 of the suction conduit 10 during declogging. Recess 131 is disposed between the first aperture 132 and the second aperture 134. Second aperture 134 may be covered by a flexible cover 162' (see FIG. 10). With reference to FIGS. 8A and 8B, second aperture 134 may include a frustoconical outer portion 160 and a cylindrical inner portion 161. The frustoconical outer portion 160 and the cylindrical inner portion 161 are configured to guide the head 14 of the suction conduit 10 into the body 130 for declogging.

Declogging assembly 120 also includes a plug 140 moveably disposed within the recess 131 of the body 130. Plug 140 defines a channel 144 that optionally connects apertures 132 and 134. FIG. 8A shows plug 140 is in its first position, wherein first aperture 132 (which connects fluid reservoir 96 to declogging assembly 120 via tube 98) is in fluid communication with the second portion 131b of recess 131. FIG. 8B shows plug 140 is in its second position, wherein first aperture 132 is in fluid communication with second aperture 134 (which is configured to fit the head 14 of suction conduit 10) via channel 144.

Plug 140 defines a luer lock portion 170 that may be a female luer lock portion that defines a recess into which a corresponding luer lock portion 182 (a male luer lock portion) of a fenestrated needle 180 of the plug 140 may be secured. In some embodiments, the plug 140 may define a male luer lock portion and fenestrated needle 180 may include a female luer lock portion. As shown in FIGS. 8A and 8B, the mating luer lock portions 170, 182 are disposed about a top portion of the channel 144 to enable fluid to flow through channel 144 and into fenestrated needle 180.

Figure 9A:
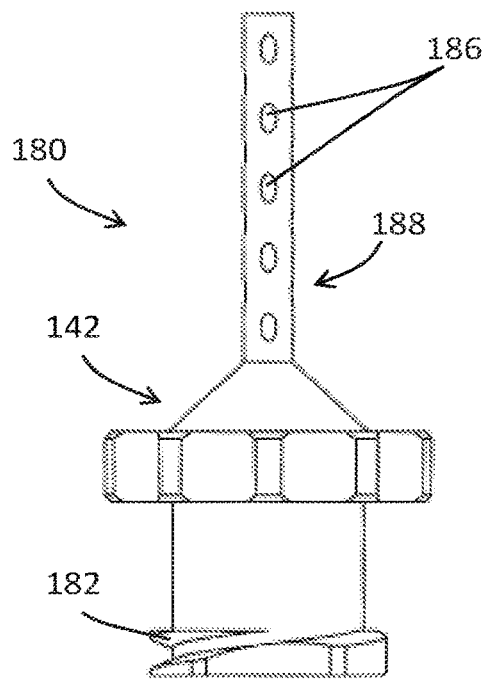
FIGS. 9A, 9B, and 9C are views of a fenestrated needle of the declogging assembly shown in FIGS. 6, 7A, 7B, 8A, and 8B.
Figure 9B:
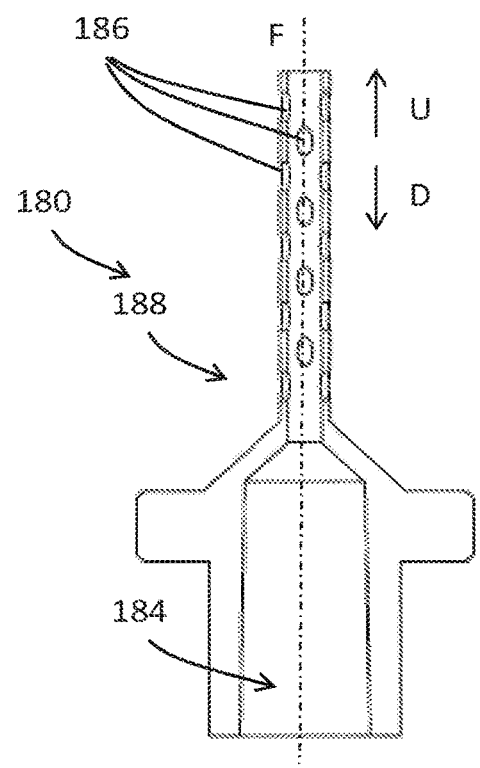
Figure 9C:
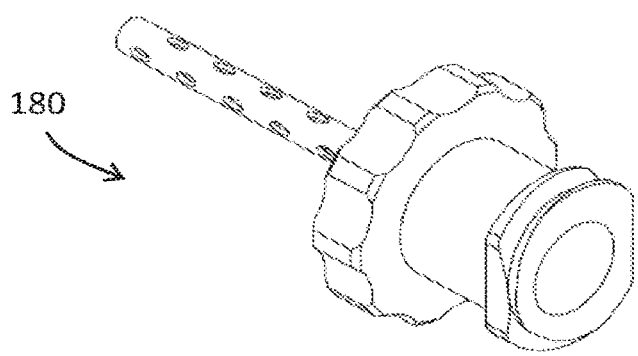

With reference to FIGS. 9A, 9B, and 9C, fenestrated needle 180 is elongate along axis F and defines a channel 184. Fenestrated needle 180 includes a fenestrated flange 188 that defines a plurality of fenestrations 186 that connect channel 184 to a surrounding environment of the fenestrated needle 180. Fenestrated needle 180 further includes a surface 142. During use, the head 14 of the suction conduit 10 is configured to contact the surface 142 to move the plug 140 from its first position to its second position. For example, the suction conduit 10 and fenestrated needle 180 may be configured such that suction conduit 10 contacts the portion of surface 142 that extends radially from axis F. Alternatively, suction conduit 10 and fenestrated needle 180 may be configured such that the suction conduit 10 contacts the frustoconical portion of surface 142. The declogging assembly further includes a biasing member 150 disposed in the second portion 131b of recess 131. Biasing member 150 may be a spring that is configured to bias the plug 140 into the first position by exerting a force in an upward direction U along axis F. Fluid from fluid reservoir 96 also exerts a biasing force in an upward direction U along axis F before plug 140 is moved to its second position and channel 144 is positioned to fluidly connect fluid reservoir 96 to second aperture 134.

Prior to insertion of the suction conduit 10, when the plug 140 is in its first position in the first portion 131a of recess 131 (shown in FIG. 8A), fluid reservoir 96 is in fluid communication with the second portion 131b of the recess 131. When a user inserts the suction conduit 10 into second aperture 134 and presses against surface 142 in a downward direction D along axis F (opposing the upward direction U), the biasing forces of biasing member 150 and the fluid may be overcome such that plug 140 moves downward into its second position in the second portion 131b of recess 131 (shown in FIG. 8B). In its second position, plug 140 enables fluid communication between first aperture 132 and second aperture 134 via channel 144, which enables vacuum force along the first direction B relative to the suction conduit 10 to pull fluid from the fluid reservoir 96, through tube 98, channel 144, and the plurality of fenestrations 186 and into the suction conduit 10. Fluid may also be pushed from the fluid reservoir 96, for example, by gravity (e.g., a saline bag hung above the declogging assembly 120). Fluid passing through the plurality of fenestrations 186 dislodges material that is clogging suction conduit 10 when the vacuum force is applied along the first direction B, may be suctioned in the second direction C away from vacuum tube connection 16 and out of the suction conduit 10 through the head 14. The material is then suctioned out of the suction conduit via vacuum assembly 90. When the user releases the downward force D on the suction conduit 10, the biasing force of the biasing member 150 returns the plug 140 to its first position in the first portion 131a of the recess 131.

Figure 10:
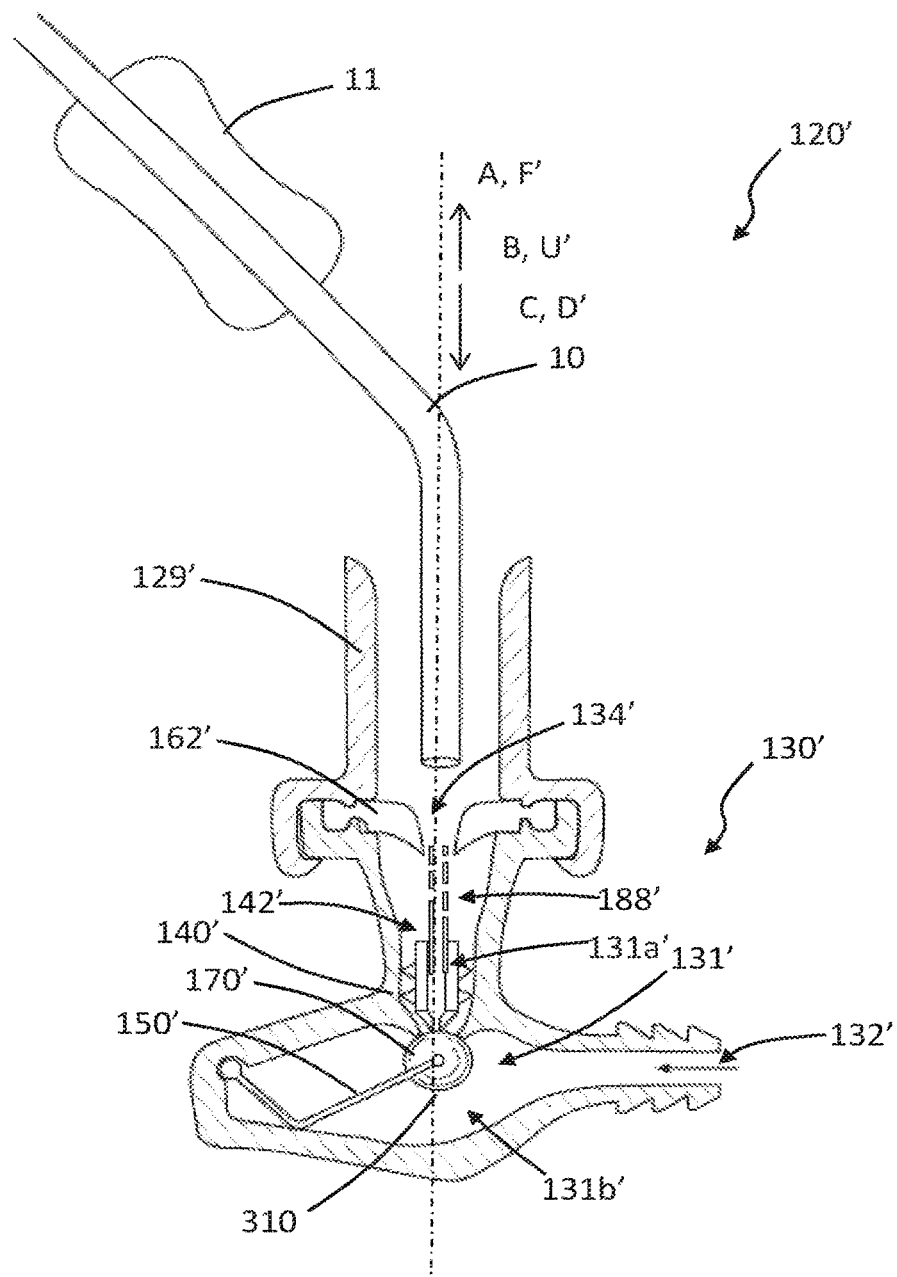
FIG. 10 is a cross-sectional view of an declogging assembly and a suction conduit with a plug of the declogging assembly in a first position.
Figure 11:
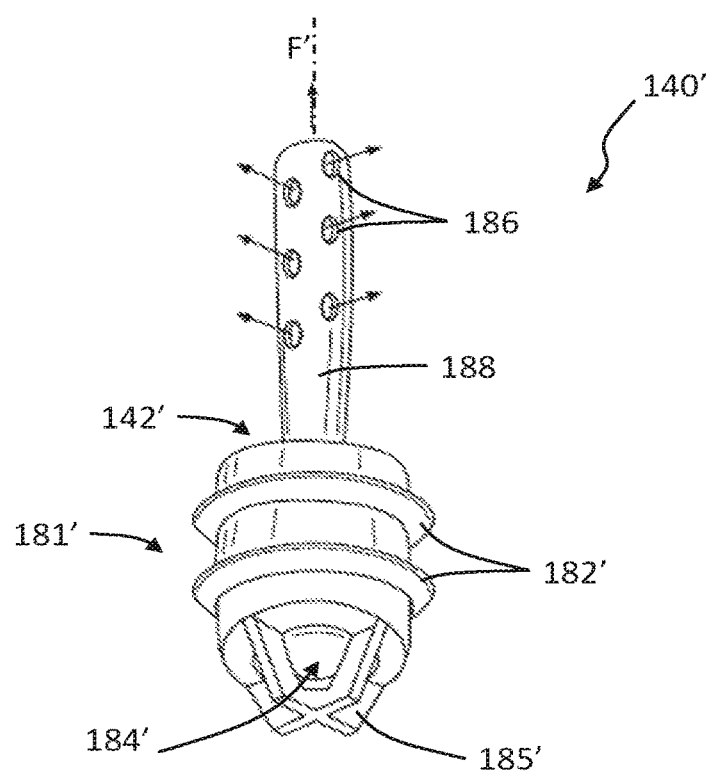
FIG. 11 is a perspective view of a plug of the declogging assembly shown in FIG. 10.

Referring now to FIGS. 10 and 11, a declogging assembly 120' is configured for use with the suction conduit 10 and the vacuum assembly 90 described in relation to FIGS. 1, 2A, and 2B, as well as the fluid reservoir 96 described in relation to FIG. 6. Declogging assembly 120' controls passage of the fluid from the fluid reservoir 96 to the suction conduit 10 so as to dislodge material affixed to suction conduit 10. Declogging assembly 120' includes a body 130'. Body 130' is elongate along an axis F' and defines a recess 131' having a first portion 131a' and a second portion 131b' disposed along the axis F'. When the head 14 of the suction conduit 10 is inserted into the body 130', axis A is parallel, or approximately parallel to axis F', such that an angle between axis A and axis F' is no more than 10°, or no more than 5°.

Body 130' defines at least two apertures that connect recess 131' to a surrounding environment of body 130'. A first aperture 132', which, for example, extends radially outward from axis F', connects the declogging assembly 120' to the fluid reservoir 96 via a tube 98. A second aperture 134' which, for example, extends axially along axis F', is configured to fit the head 14 of the suction conduit 10 during declogging. Recess 131' is disposed between the first aperture 132' and the second aperture 134'. Second aperture 134' may include a frustoconical portion 160'. The frustoconical portion 160' is configured to guide the head 14 of the suction conduit 10 into the body 130' for declogging. Second aperture 134' may be covered by a flexible cover 162'. Flexible cover 162' minimizes flow into and out of body 130' through second aperture 134'. A splash guard 129' may be disposed above second aperture 134', which defines a channel through which suction conduit 10 passes to enter second aperture 134'.

Declogging assembly 120' also includes a plug 140' moveably disposed within the recess 131' of the body 130'. Plug 140' has a base portion 170' that may, for example, be spherically shaped. FIG. 10 shows plug 140' is in its first position, wherein first aperture 132' (which connects fluid reservoir 96 to declogging assembly 120' via tube 98) is in fluid communication with the second portion 131b' of recess 131'. Plug 140' may also be disposed is in its second position, wherein first aperture 132' is in fluid communication with second aperture 134' (which is configured to fit the head 14 of suction conduit 10) via recess 131'.

With reference to FIG. 11, plug 140' is elongate along axis F' and further defines a middle portion 181' that includes seals 182'. Seals 182' are configured to minimize flow from the second portion 131b' to the first portion 131a' of the recess 131'. Plug 140' also defines a channel 184' and includes a fenestrated flange 188' that defines a plurality of fenestrations 186' that connect channel 184' to a surrounding environment of the fenestrated needle 180'. Plug 140' further includes a surface 142'. During use, the head 14 of the suction conduit 10 is configured to contact the surface 142' to move the plug 140 from its first position to its second position. For example, the suction conduit 10 and fenestrated needle 180 may be configured such that suction conduit 10 contacts the portion of surface 142' that extends radially from axis F'. Plug 140' also includes a spacer 185' disposed between the base portion 170' and the middle portion 181'.

The declogging assembly 120' further includes a biasing member 150' disposed in the second portion 131b' of recess 131'. Biasing member 150' may be a spring that is configured to bias the plug 140' into the first position by exerting a force in an upward direction U' along axis F'. Fluid from fluid reservoir 96 also exerts a biasing force in an upward direction U' along axis F' before plug 140' is moved to its second position in which plug 140' is positioned to fluidly connect fluid reservoir 96 to second aperture 134'.

Prior to insertion of the suction conduit 10, when the plug 140' is in its first position in the first portion 131a' of recess 131' (shown in FIG. 10), fluid reservoir 96 is in fluid communication with the second portion 131b' of the recess 131'. When a user inserts the suction conduit 10 into second aperture 134' and presses against surface 142' in a downward direction D' along axis F' (opposing the upward direction U'), the biasing forces of biasing member 150' and the fluid may be overcome such that plug 140' moves downward into its second position in the second portion 131b' of recess 131'. In its second position, plug 140' enables fluid communication between first aperture 132' and second aperture 134' via recess 131', which enables vacuum force along the first direction B relative to the suction conduit 10 to pull fluid from the fluid reservoir 96, through tube 98, channel 144, and the plurality of fenestrations 186' and into the suction conduit 10. Fluid may also be pushed from the fluid reservoir 96, for example, by gravity (e.g., a saline bag hung above the declogging assembly 120'). Fluid passing through the plurality of fenestrations 186' dislodges material that is clogging suction conduit 10 when the vacuum force is applied along the first direction B, may be suctioned in the second direction C away from vacuum tube connection 16 and out of the suction conduit 10 through the head 14. The material is then suctioned out of the suction conduit via vacuum assembly 90. When the user releases the downward force D' on the suction conduit 10, the biasing force of the biasing member 150' returns the plug 140' to its first position in the first portion 131a' of the recess 131'.

Figure 12:
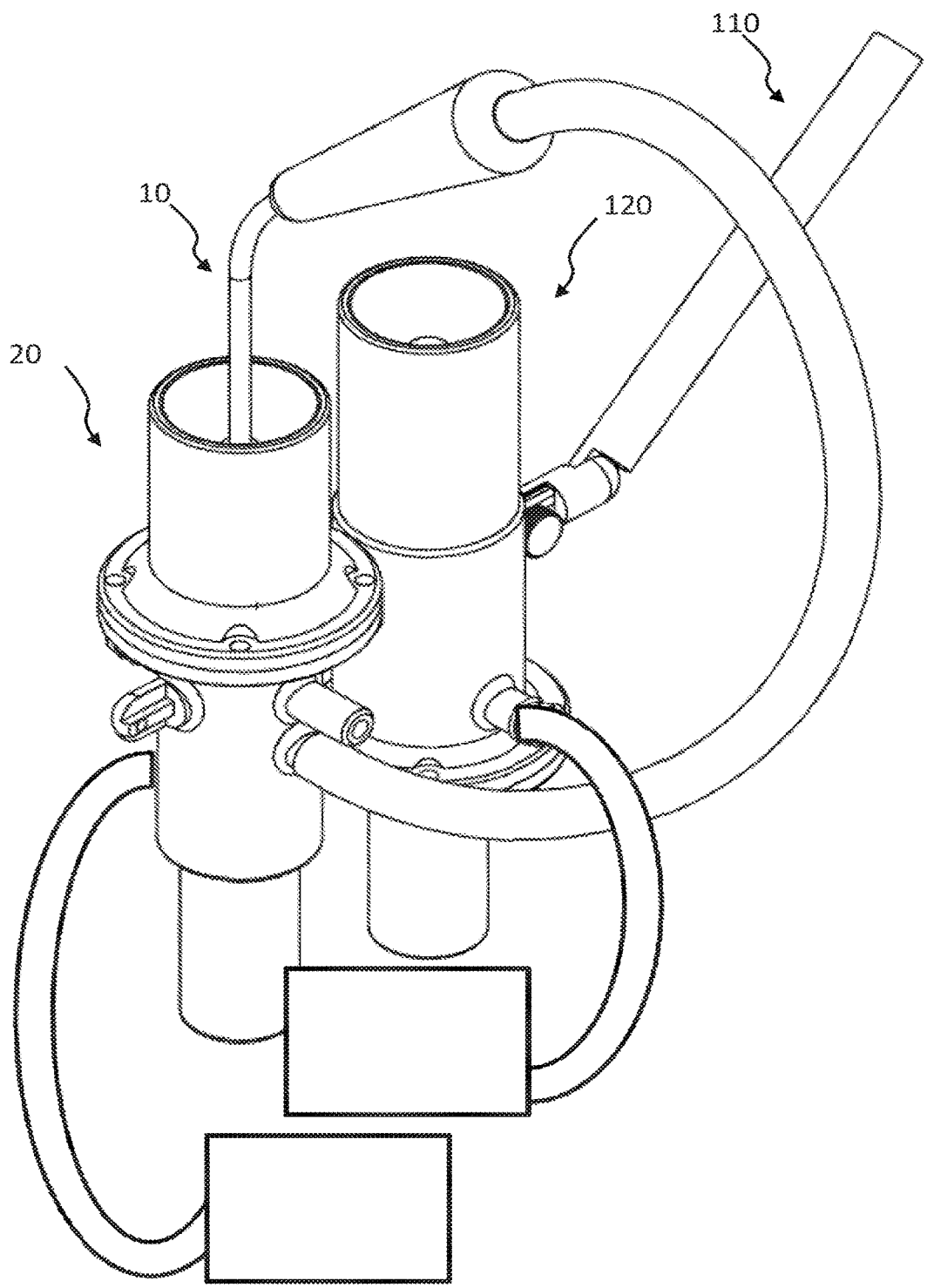
FIG. 12 is a perspective view of the declogging assembly shown in FIGS. 1, 2A, 2B, 3A, and 3B, and the declogging assembly shown in FIGS. 6, 7A, 7B, 8A, and 8B connected to a mounting assembly.
Figure 13:
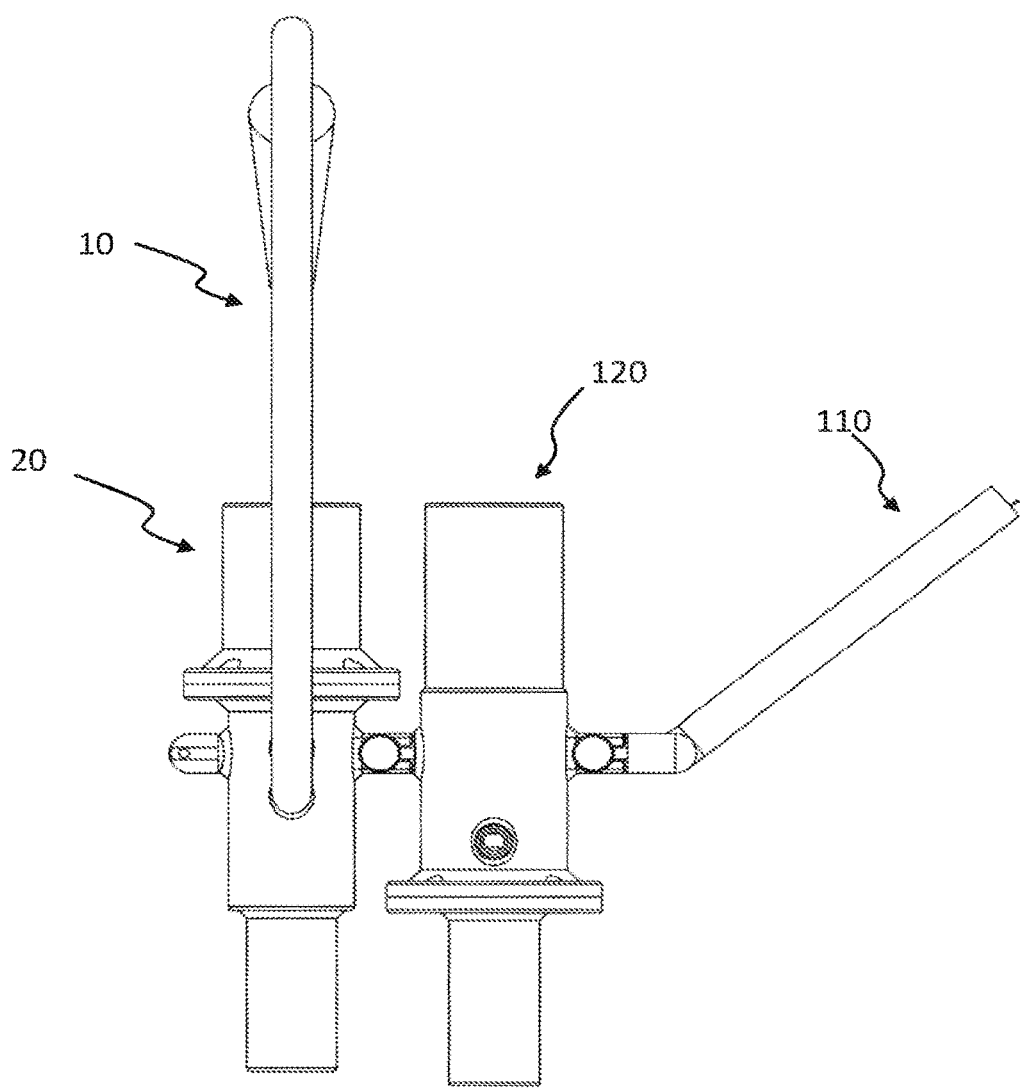
FIG. 13 is a side view of the declogging assembly shown in FIGS. 1, 2A, 2B, 3A, 3B and 12, and the declogging assembly shown in FIGS. 6, 7A, 7B, 8A, 8B and 12 connected to the mounting assembly shown in FIG. 12.

With reference now to FIGS. 12 and 13, the declogging assemblies 20, 120 shown in FIGS. 1, 2A, 2B, 3A, 3B and FIGS. 6, 7A, 7B, 8A, 8B, 9A, 9B, 9C and described above are depicted affixed to one another and affixed to a mounting bar 110. Mounting bar 110 is configured for attachment, for example, to a surgical cot. Mounting bar 110 may be rotatable in relation to declogging assemblies 20, 120. For example, mounting bar 110 may be rotatable up and down in relation to axes E, F. Mounting bar 110 may also be rotatable about an axis that extends parallel to axes E, F. Declogging assemblies 20, 120 may also be rotatable relative to each other.

In use, suction conduit 10 may be employed to remove material from the operative field during surgery. In order to remove material from the operative field, as described above, the plug 40 of declogging assembly 20 is biased into its first position so as to provide the vacuum force to the suction conduit 10 along first direction B. During the course of using the suction conduit 10, it will become clogged with material. In order to dislodge this material from the suction conduit 10, two techniques may be employed in any order. For example, suction conduit 10 may be inserted into third aperture 36 so as to reverse the vacuum force in suction conduit 10 and pull material in second direction C through second channel 46 and first aperture 32 of the declogging assembly 20. After or before reversing the vacuum force using declogging assembly 20, declogging assembly 120 may be used to irrigate suction conduit 10 with, for example, saline. Irrigation of suction conduit 10 may also dislodge material affixed to suction conduit 10. Declogging assemblies 20, 120 may be used in an alternating fashion, one after another, until the suction conduit 10 is substantially free of material.

What is claimed is:

1. A declogging assembly configured for use with a suction conduit, the assembly comprising:
   a body, the body defining a first aperture and a second aperture;
   a plug disposed within the body, the plug further defining a channel, the channel configured in a first state to disable fluid communication between the first aperture and the second aperture, and in a second state to enable fluid communication between the first aperture and the second aperture; and
a biasing member configured to bias the channel into the first state,
   wherein the plug further comprises a needle, the needle constituting a portion of the channel.

2. The declogging assembly of claim 1, wherein at least a portion of the second aperture has a frustoconical shape.

3. The declogging assembly of claim 1, further comprising a flexible cover that extends at least partially over the second aperture.

4. The declogging assembly of claim 1, wherein the plug includes a fenestrated flange that defines a plurality of fenestrations.

5. A declogging assembly configured for use with a suction conduit, the assembly comprising:
   a body, the body defining a first aperture and a second aperture;
   a plug disposed within the body, the plug further defining a channel, the channel configured in a first state to disable fluid communication between the first aperture and the second aperture, and in a second state to enable fluid communication between the first aperture and the second aperture; and a biasing member configured to bias the channel into the first state, wherein the plug further comprises a fenestrated needle, the fenestrated needle constituting a portion of the channel.

6. The declogging assembly of claim 5, wherein at least a portion of the second aperture has a frustoconical shape.

7. The declogging assembly of claim 5, further comprising a flexible cover that extends at least partially over the second aperture.

8. The declogging assembly of claim 5, wherein the plug includes a fenestrated flange that defines a plurality of fenestrations.

\* \* \* \* \*